(12) United States Patent
Bell et al.

(10) Patent No.: US 12,171,947 B2
(45) Date of Patent: Dec. 24, 2024

(54) TUBING ASSEMBLY FOR PATIENT INTERFACE DEVICE AND ELEMENTS FOR IMPROVING THE FIT AND FEEL OF SUCH ASSEMBLY

(71) Applicant: KONINKLIJKE PHILIPS N.V., Eindhoven (NL)

(72) Inventors: Adam Levern Bell, Pittsburgh, PA (US); Kevin Daniel Himes, Irwin, PA (US); Jonathan Sayer Grashow, Pittsburgh, PA (US); Daniel Steed, Pittsburgh, PA (US); Elizabeth Eury, Latrobe, PA (US); Richard Thomas Haibach, Verona, PA (US); Stephen Hlopick, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 251 days.

(21) Appl. No.: 17/587,323

(22) Filed: Jan. 28, 2022

(65) Prior Publication Data
US 2022/0152334 A1 May 19, 2022

Related U.S. Application Data

(62) Division of application No. 15/578,805, filed as application No. PCT/IB2016/053025 on May 24, 2016.

(60) Provisional application No. 62/171,530, filed on Jun. 5, 2015.

(51) Int. Cl.
*A61M 16/06* (2006.01)
*A61M 16/08* (2006.01)

(52) U.S. Cl.
CPC .... *A61M 16/0683* (2013.01); *A61M 16/0875* (2013.01); *A61M 16/0605* (2014.02)

(58) Field of Classification Search
CPC .......... A61M 16/0683; A61M 16/0875; A61M 16/0605; A61M 16/0666; A61M 16/08; A61M 16/06
See application file for complete search history.

(56) References Cited

U.S. PATENT DOCUMENTS

| | | | |
|---|---|---|---|
| 4,878,491 A * | 11/1989 | McGilvray, III | B63C 11/205 128/201.11 |
| 8,783,298 B2 | 7/2014 | Zucker | |
| 2006/0180151 A1 | 8/2006 | Rinaldi | |
| 2006/0196511 A1* | 9/2006 | Lau | A61M 16/0666 128/207.18 |
| 2006/0278232 A1 | 12/2006 | Nichols | |
| 2007/0163600 A1 | 7/2007 | Hoffman | |

(Continued)

*Primary Examiner* — Bradley H Philips
*Assistant Examiner* — Savannah L Gabriel
(74) *Attorney, Agent, or Firm* — Michael W. Haas

(57) ABSTRACT

A tubing assembly for use with a patient interface device includes a manifold portion structured to be coupled to a conduit carrying a flow of breathing gas and a number of tubular portions. Each tubular portion extends from the manifold portion to a distal end which is structured to be coupled to the patient interface device. Each tubular portion is structured to communicate the flow of breathing gas from the manifold portion to the patient interface device. Each tubular portion comprises an adjustment element which provides for a characteristic of the tubular portion to be selectively varied.

2 Claims, 15 Drawing Sheets

(56) References Cited

U.S. PATENT DOCUMENTS

| | | | | |
|---|---|---|---|---|
| 2008/0060649 | A1* | 3/2008 | Veliss | A61M 16/06 |
| | | | | 128/207.18 |
| 2009/0199856 | A1* | 8/2009 | Berlin | A61M 16/0683 |
| | | | | 128/206.13 |
| 2011/0247619 | A1 | 10/2011 | Formica | |
| 2012/0204880 | A1* | 8/2012 | Smith | A61M 16/06 |
| | | | | 128/206.24 |
| 2012/0325219 | A1* | 12/2012 | Smith | A61M 16/0875 |
| | | | | 128/205.25 |
| 2014/0137870 | A1 | 5/2014 | Barlow | |
| 2014/0311492 | A1 | 10/2014 | Stuebiger | |
| 2014/0330254 | A1 | 11/2014 | Rosenberger | |
| 2015/0083136 | A1 | 3/2015 | Grashow | |
| 2016/0095996 | A1 | 4/2016 | Gusky | |

\* cited by examiner

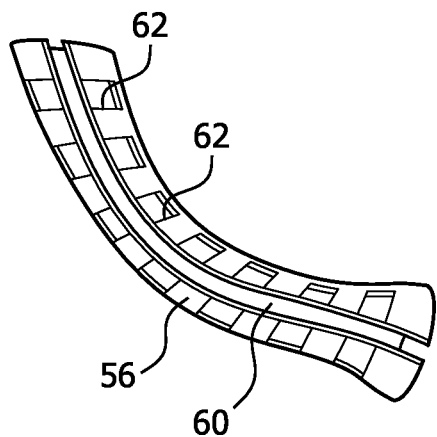 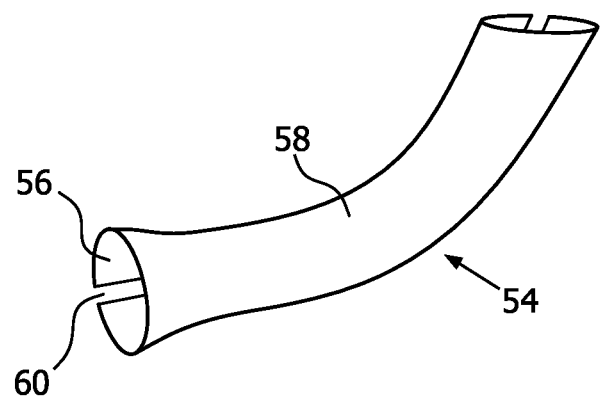
FIG. 12A    FIG. 12B
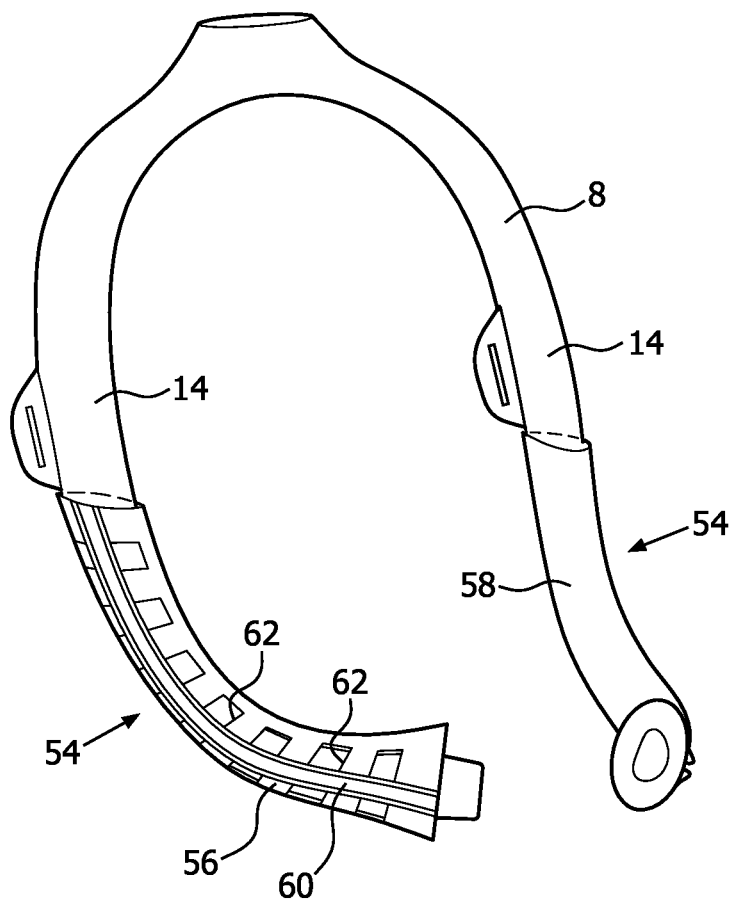
FIG. 13

TUBING ASSEMBLY FOR PATIENT INTERFACE DEVICE AND ELEMENTS FOR IMPROVING THE FIT AND FEEL OF SUCH ASSEMBLY

CROSS-REFERENCE TO RELATED APPLICATIONS

The present application is a divisional of U.S. patent application Ser. No. 15/578,805, filed Dec. 1, 2017, which is a U.S. National Stage under 35 U.S.C. § 371 of International Patent Application No. PCT/IB2016/053025, filed May 24, 2016, which claims the benefit of U.S. Provisional Application No. 62/171,530, filed on Jun. 5, 2015, the contents of which are herein incorporated by reference.

BACKGROUND OF THE INVENTION

1. Field of the Invention

The present invention pertains to tubing assemblies for patient interface devices and enhancements thereto.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from a pressure/flow generating device to the airway of the patient. It is known to maintain such devices on the face of a wearer by a headgear having one or more straps adapted to fit over/around the patient's head. Because such patient interface devices are typically worn for an extended period of time, it is important for the headgear to maintain the mask component of the device in a tight enough seal against the patient's face without discomfort.

A number of known patient interface devices provide airflow to the patient through the headgear via one or more delivery conduits that wrap around portions of the patient's head as part of the headgear. That is, the headgear includes a tubing assembly with a manifold. The manifold is coupled to, and in fluid communication with, a delivery conduit. The delivery conduit is further coupled to, and in fluid communication with, the pressure/flow generating device. Such known patient interface devices, however, have a number of drawbacks.

For example, due to the functionality of the headgear in providing airflow to the patient, the sizing options of such headgear is typically limited and generally not customizable to a particular patient.

SUMMARY OF THE INVENTION

Accordingly, it is an object of the present invention to provide a tubing assembly for use with a patient interface device in delivering a flow of breathing gas to the airway of a user. The tubing assembly comprises: a manifold portion structured to be disposed generally at the top of the user's head and adapted to be coupled to a conduit carrying the flow of breathing gas; and a number of tubular portions, each tubular portion extending from the manifold portion to a distal end which is structured to be coupled to the patient interface device, each tubular portion being structured to communicate the flow of breathing gas from the manifold portion to the patient interface device. Each tubular portion comprises an adjustment element which provides for a characteristic of the tubular portion to be selectively varied.

The characteristic may comprise one or more from the group consisting of: size and feel.

The adjustment element may comprise an adjustment portion which extends from the distal end of each tubular portion, each adjustment portion comprising a plurality of flared segments, each of generally similar size and shape, which are structured to engage a correspondingly shaped receiving portion formed in an opening of the patient interface device.

The adjustment element may comprise a number of tubular adjustment members, each comprising: a body having a predetermined length and defining a hollow passage therethrough; a protruding portion extending from a first end of the body, which is of similar form as one of the distal end of the tubular portion or an end portion of the patient interface device; and a receptacle portion extending from an opposite second end of the body which is of similar form as the other one of the distal end of the tubular portion or the end portion of the patient interface device. Each protruding portion is structured to be readily snap fit into the receptacle portion of another tubular adjustment member.

The adjustment element may comprise an adjustment portion disposed in a tubular portion, the adjustment portion comprising: a stretch portion formed as a portion of the tubular portion, the stretch portion being structured to elongate more readily than the tubular portion; and a support element disposed adjacent the stretch portion.

The support element may comprise a generally helically shaped member.

Each tubular portion may comprise a mounting tab adjustably coupled thereto, each mounting tab being structured to receive a portion of a strap member for securing the tubing assembly to the head of the user. Each mounting tab may be slidably coupled to one of the tubular portions via an interaction of a channel member and a rail member.

The adjustment element may comprise an over-support member which is generally fit over one of the tubular portions, the over-support member comprising: a channel defining an opening along the entire length thereof; and a patient facing portion including a surface texture or material which differs from the surface texture or material of the tubular portion. The channel may comprises a number of cut-outs.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 12A and 12B, respectively, show views of the outward and patient facing sides of an over-support member in accordance with an exemplary embodiment of the present invention;

FIG. 13 is an isometric view of the over-support member of FIGS. 12A and 12B shown disposed on a tubing assembly in accordance with an exemplary embodiment of the present invention;

DETAILED DESCRIPTION OF EXEMPLARY EMBODIMENTS

Figure 1A:
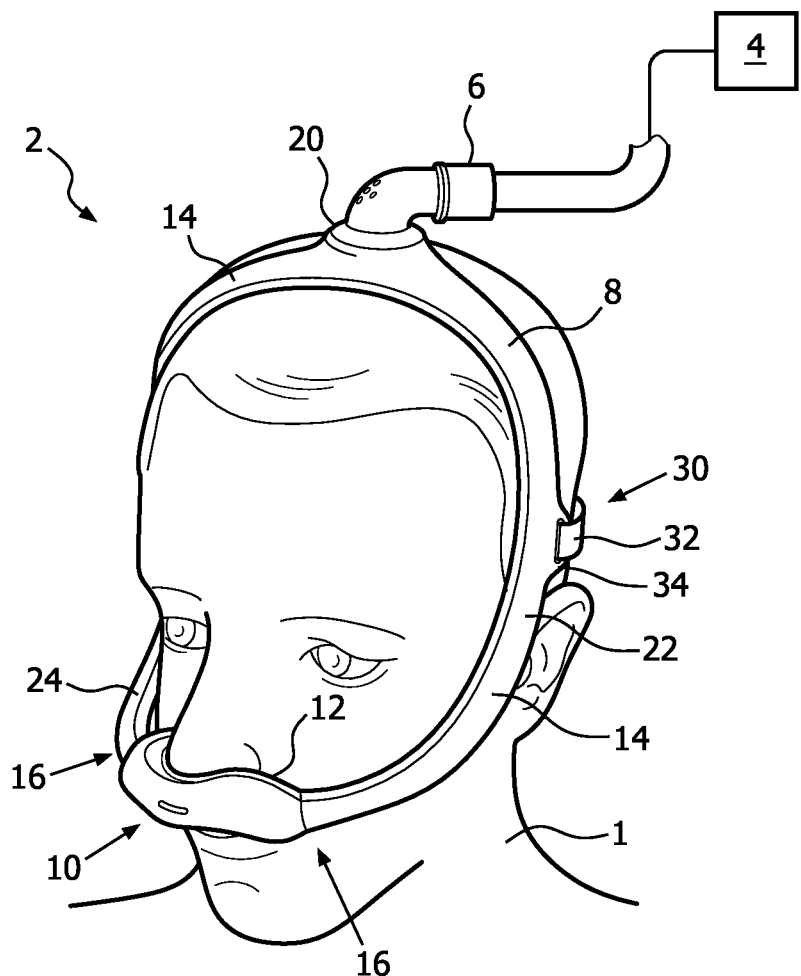
FIG. 1A is a partially schematic view of a respiratory interface system in accordance with an exemplary embodiment of the present invention shown disposed on the head of a patient.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the statement that two or more parts or components "engage" one another shall means that the parts exert a force against one another either directly or through one or more intermediate parts or components. As used herein, the word "unitary" means a component is created as a single piece or unit. That is, a component that includes pieces that are created separately and then coupled together as a unit is not a "unitary" component or body. As used herein, the term "number" shall mean one or an integer greater than one (i.e., a plurality).

As used herein, a "coupling assembly" includes two or more couplings or coupling components. The components of a coupling or coupling assembly are generally not part of the same element or other component. As such the components of a "coupling assembly" may not be described at the same time in the following description.

As used herein, a "coupling" is one element of a coupling assembly. That is, a coupling assembly includes at least two components, or coupling components, that are structured to be coupled together. It is understood that the elements of a coupling assembly are compatible with each other. For example, in a coupling assembly, if one coupling element is a snap socket, the other coupling element is a snap plug.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together or "snuggly correspond." In that situation, the difference between the size of the components is even smaller whereby the amount of friction increases. If the element defining the opening and/or the component inserted into the opening is/are made from a deformable or compressible material, the opening may even be slightly smaller than the component being inserted into the opening. This definition is further modified if the two components are said to "substantially correspond." "Substantially correspond" means that the size of the opening is very close to the size of the element inserted therein. That is, not so close as to cause substantial friction, as with a snug fit, but with more contact and friction than a "corresponding fit," i.e. a "slightly larger" fit.

Figure 1B:
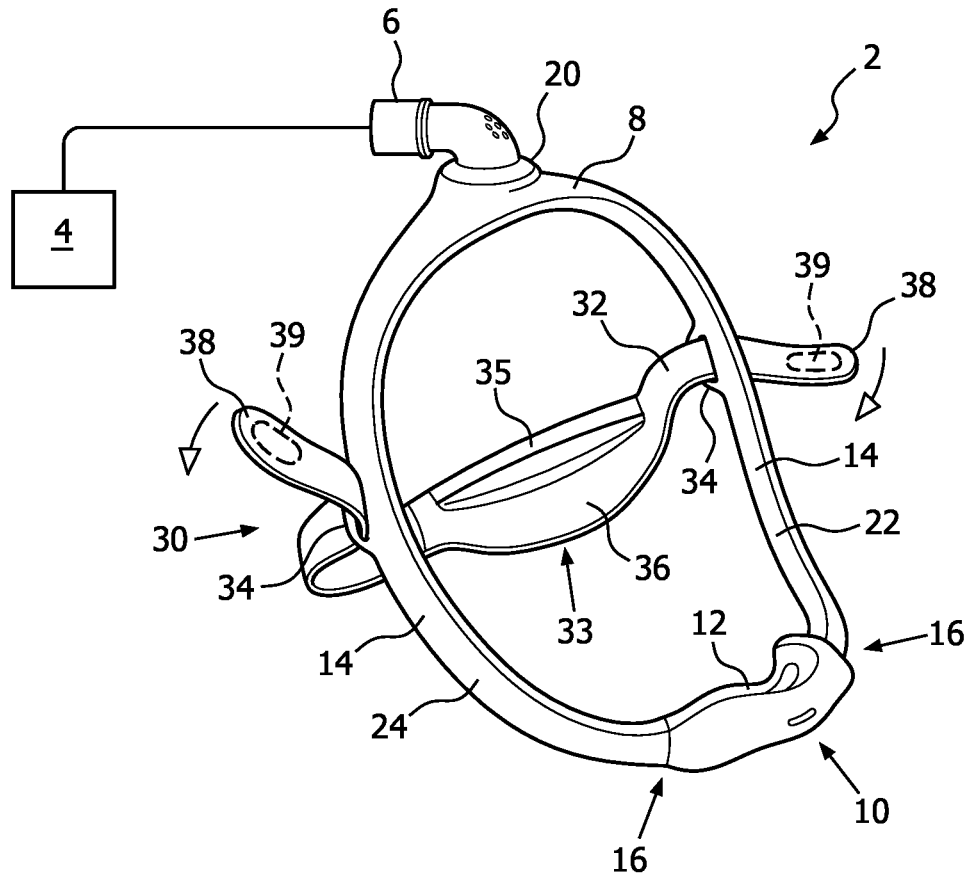
FIG. 1B is another partially schematic view of the respiratory interface system of FIG. 1A shown without a patient.

As shown in FIG. 1A, a respiratory interface system 2 is adapted to provide a regimen of respiratory therapy to a patient 1 according to one exemplary embodiment of the present invention. Referring to FIGS. 1A and 1B, respiratory interface system 2 includes a pressure generating device 4 (shown schematically), a delivery conduit 6 fluidly coupled to a tubing assembly 8, and a patient interface device 10 fluidly coupled to tubing assembly 8. Pressure generating device 4 is structured to generate a flow of positive pressure breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, PA), and auto-titration pressure support devices. Delivery conduit 6 is structured to communicate the flow of breathing gas from pressure generating device 4 to patient interface device 10 through tubing assembly 8 (the breathing gas enters at the top of the head of patient 1). Delivery conduit 6, tubing assembly 8 and patient interface device 10 are often collectively referred to as a patient circuit.

Patient interface device 10 includes a patient sealing element 12. In an exemplary embodiment, such as illustrated in FIGS. 1A and 1B, patient sealing element 12 is a nasal cushion made of a soft, flexible material, such as, without limitation, silicone, an appropriately soft thermoplastic elastomer, a closed-cell foam, or any other suitable material or combination of such materials. It is to be appreciated, however, that any type of patient sealing element, such as a nasal/oral mask, a nasal pillow or a full face mask, which facilitates the delivery of the flow of breathing gas to the airway of a patient, may be used as sealing element 12 while remaining within the scope of the present invention.

Figure 2:
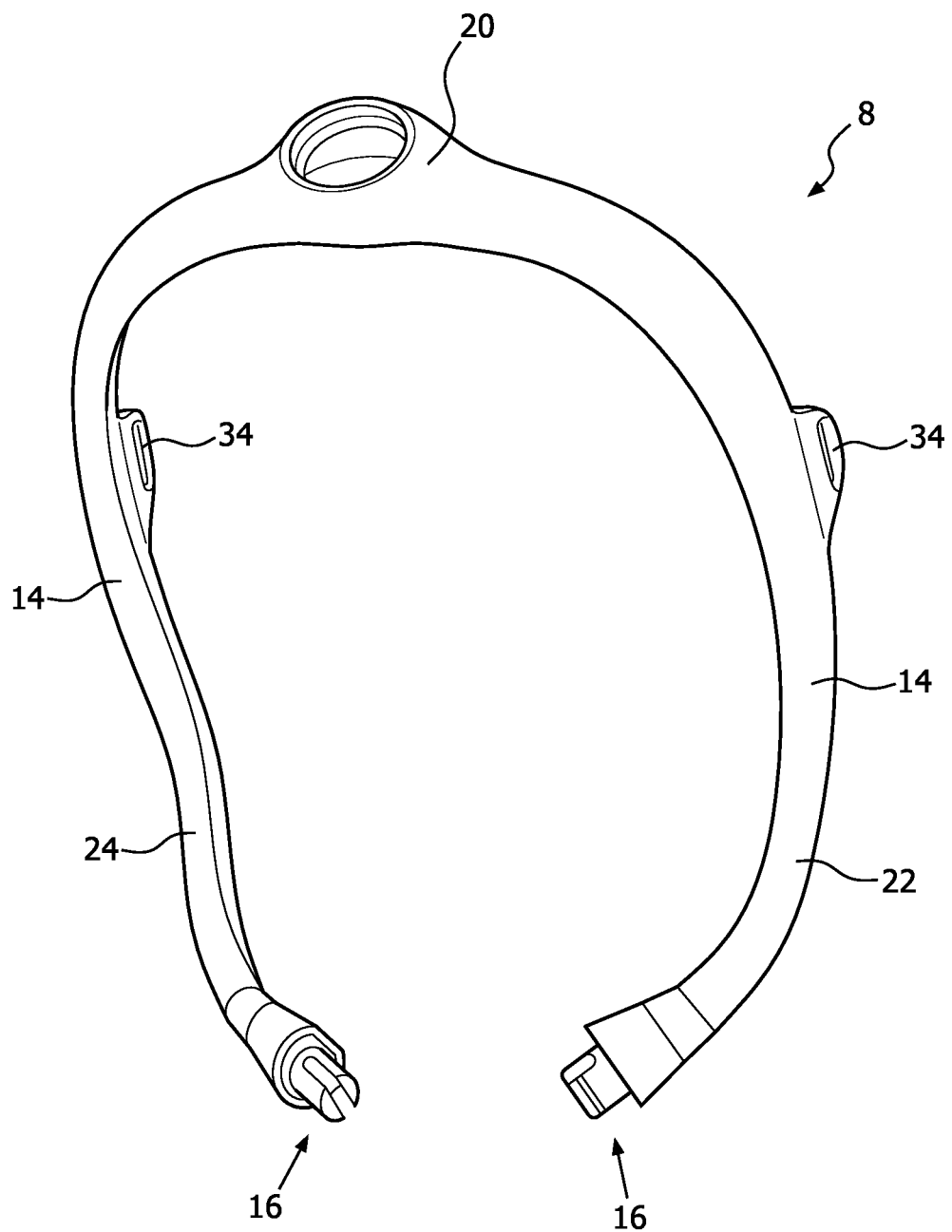
FIG. 2 is an isometric view of a tubing assembly in accordance with an exemplary embodiment of the present invention.

Continuing to refer to FIGS. 1A and 1B, as well as FIG. 2, tubing assembly 8 includes a number of tubular portions 14 which each extend from a manifold portion 20 to a distal end 16. Distal end 16 of each tubular portion 14 is coupled to, and in fluid communication with, patient interface device 10. In exemplary embodiments tubing assembly 8 is made from plastic and/or silicone and may be formed as a single unitary member or alternately may be formed from a number of separately formed components that are then coupled together via a suitable process. Tubing assembly 8 may also be formed from other suitable materials (e.g., fabric) without varying from the scope of the present invention.

Manifold portion 20 is structured to be coupled to delivery conduit 6, such as via an elbow or other suitable coupling member. As shown in FIG. 1A, when tubing assembly 8 is disposed on the head of patient 1, manifold portion 20 is disposed generally at the top of the head of patient 1 and tubular portions 14 extend generally downward from manifold portion 20 to sealing element 12 of patient interface device 10. In the exemplary embodiment illustrated in FIGS. 1A, 1B and 2, there are two tubular portions 14, namely left and right side arms 22, 24, which each have a generally non-circular cross-section. That is, each tubular portion 14 is not substantially circular. In another exemplary embodiment, not shown, tubing assembly 8 includes a single tubular portion 14 that extends centrally, i.e. from manifold portion 20 generally over the patient's forehead and nose, to sealing element 12.

In an exemplary embodiment, each tubular portion 14 has a generally D-shaped cross-section wherein the generally flat side of the D-shape is disposed adjacent the user's head while the curved portion faces away from the user's head. As shown in FIG. 1A, tubular portions 14, i.e. left and right side arms 22, 24, encircle, or partially encircle, the head of patient 1. Accordingly, it is to be appreciated that tubing assembly 8, as a result of its basic structure and positioning, generally functions not only as a portion of the supply conduit for providing gas to/from patient interface device 10, but also generally functions as a frame, securing patient interface device 10 to the head of patient 1.

Figure 3:
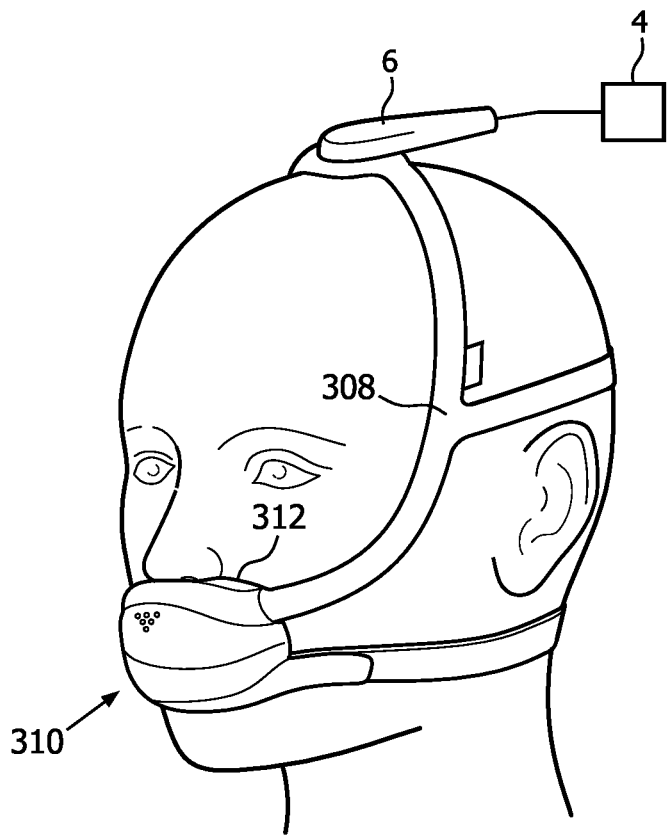
FIGS. 3-4 are partially schematic views of respiratory interface systems in accordance with exemplary embodiments of the present invention shown disposed on the head of a patient.
Figure 4:
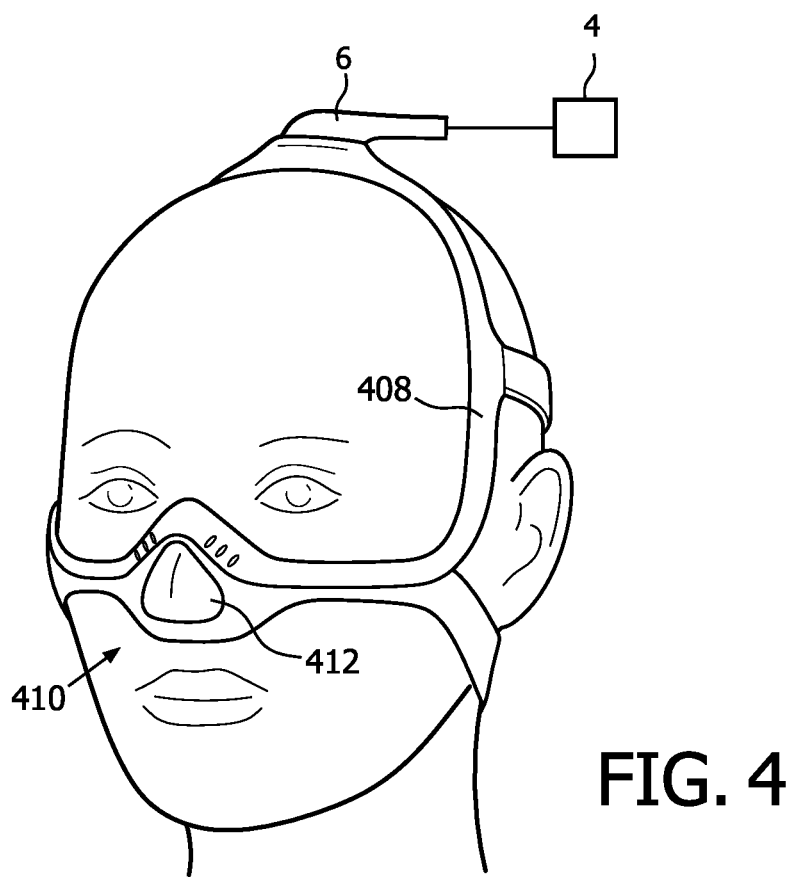
Figure 5:
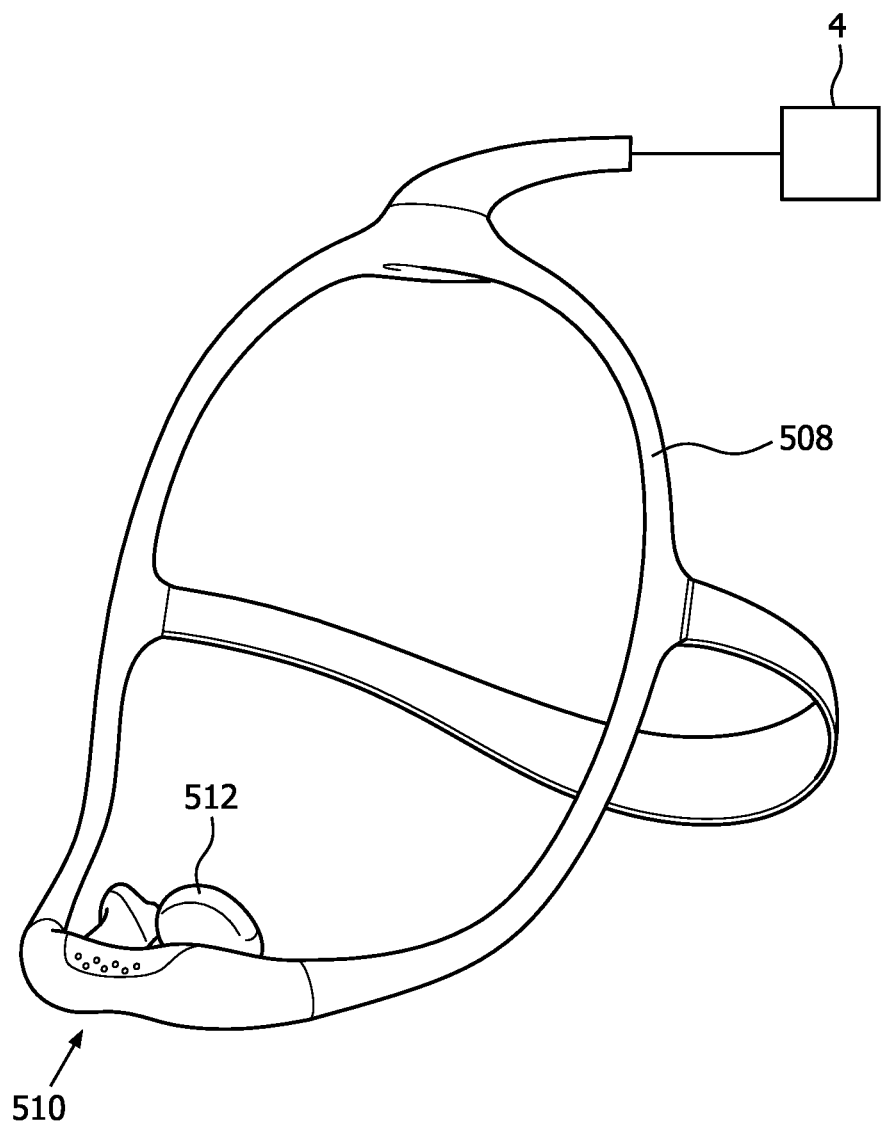
FIG. 5 is a partially schematic view of a respiratory interface system in accordance with an exemplary embodiment of the present invention.

FIGS. 3-5, respectively, show exemplary embodiments of other tubing assemblies 308, 408 and 508 of similar construction as tubing assembly 8 except used in conjunction with patient interface devices 310, 410 and 510 having sealing elements 312, 412 and 512 in the form of: a full face under the nose cushion (FIG. 3), a nasal (over the nose) cushion (FIG. 4) and individual nasal pillows (FIG. 5).

Figure 1C:
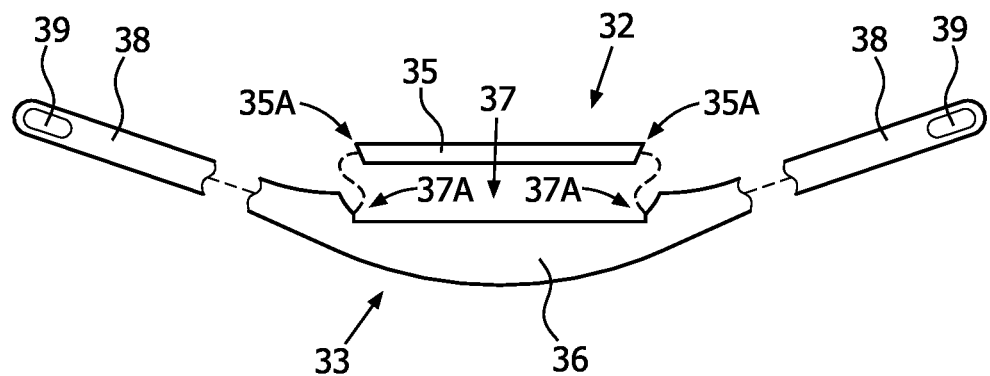
FIG. 1C is an exploded view of a rear strap of the respiratory interface system of FIGS. 1A and 1B showing the outward facing side.

Referring again to FIG. 1A, in order to help secure patient interface device 10 and tubing assembly 8 to the head of patient 1, tubing assembly 8 may further include a support assembly 30. As shown in FIGS. 1A-1C, support assembly 30 includes a rear strap 32 coupled to left and right side arms 22, 24 which also encircles, or partially encircles, the head of patient 1. That is, rear strap 32 is structured to engage the rear of the head of patient 1. In an exemplary embodiment of the present invention, rear strap 32 is structured to fit generally just below the occipital bone of a patient. Rear strap 32 may be coupled to each of left and right side arms 22, 24 by a mounting tab 34 disposed on each tubular portion 14. As shown in the exemplary embodiment of FIGS. 1A, 1B and 2, each mounting tab 34 may be fixed with respect to each tubular portion 14. In such arrangements, each mounting tab 34 may be formed as an integral portion of each tubular portion or may be formed separately therefrom and then rigidly coupled thereto. In exemplary embodiments of the present invention, mounting tab 34 has been formed from silicone, however, it is to be appreciated that other suitable materials (e.g., without limitation plastic or fabric) may be employed without varying from the scope of the present invention.

Referring to FIGS. 1B and 1C, rear strap 32 includes a central strap portion 33 disposed between two end portions 38. Each end portion 38 is structured to engage and be selectively fastened to one of tubular portions 14, such as via one of mounting tabs 34. Central strap portion 33 includes an upper strap portion 35 and a lower strap portion 36. Upper strap portion 35 is generally coupled in a notched portion 37 formed in lower strap portion 36. More particularly, each end 35A of upper strap portion 35 is fixedly coupled to a respective end 37A of notched portion 37. In an exemplary embodiment, ends 35A of upper strap portion 35 are coupled to lower strap portion 36 generally at an angle to allow rear strap 32 to more naturally conform to the back of a patient's head. Such coupling of ends 35A of upper strap portion 35 to ends 37A of notched portion may be accomplished via stitching or other suitable manner.

In an exemplary embodiment, both lower strap portion 36 and end portions 38 are produced as three layer laminations, with the patient facing portion of lower strap portion 36 being a closed cell foam and the patient facing portion of end portions 38 being a Lycra® material. The closed cell foam coating on the patient facing side of lower strap portion 36 has a generally high coefficient of friction and is able to conform to the patient's head, thus better allowing rear strap 32 to stay in place while in use. The Lycra® material on the patient contacting side of end portions 38 is soft and conforming to be comfortable on the side of a patient's head and generally smoothly passes through mounting tabs 34 without undesirably snagging the patient's hair. In such exemplary embodiment the middle layer of both portions 36 and 38 is an open cell foam which adds pliable body and integrity to rear strap 32 and the outside layer opposite of the patient facing side is UBL (unbroken loop). In order to provide for releasable fastening of strap member 32 to tubular portions 14, each end portion 38 includes a section of hook tab material 39 (e.g., Velcro®) which is positioned and structured to engage the outward facing UBL material when each end portion 38 is folded back toward central strap portion 33 such as shown by the arrows in FIG. 1B.

In an exemplary embodiment, upper strap portion 35 is formed from an elastic fabric (e.g., without limitation, spandex), but may also be formed from other fabrics, silicone, plastics, or any other suitable material or combination of materials such that upper strap portion 35 generally exhibits the properties of an elastic strap that is typically easy to elongate, but has great recovery properties. It is to be appreciated that such exemplary materials are provided for example purposes only and that strap member 32 may be formed from other materials without varying from the scope of the present invention.

In an exemplary embodiment, upper strap portion 35 is shorter than notched portion 37 of lower strap portion 36. This ensures that no matter the shape of the patient's head, upper strap portion 35 will engage first and then elongate until lower strap portion 36 engages the back of the patient's head. Such arrangement puts both straps in tension and provides a combination of forces and friction vectors that increases the stability of rear strap 32, and thus also tubing assembly 8, on the head of a patient. Upper strap portion 35 can also be positioned higher or lower on the patient's head in order to capture different features on the back of the head, and/or patient's with longer hair can pull hair between upper strap portion 35 and lower strap portion 36 to help keep strap 32 in place.

As shown in FIG. 1C, each end portion 38 may be formed separately from central strap portion 33 and then fixedly coupled to central strap portion 38. Such coupling of end portions 38 to central strap portion may be accomplished via welding or other suitable generally permanent manner, or hooked on through a non-permanent method. Alternatively, end portions 38 may be formed integrally with lower strap portion 36 such that the laminate including the open cell foam core and UBL material disposed on the outward facing side of the open cell foam continuously extend generally the entire length of rear strap 32.

It is to be appreciated that strap member 32 is provided for exemplary purposes only and that strap members of other design and/or construction may be employed without varying from the scope of the present invention.

Figure 6:
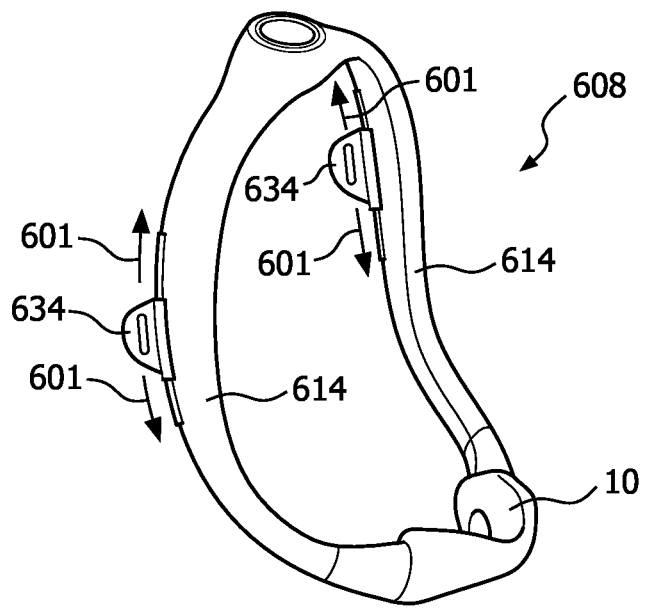
FIG. 6 is an isometric view of a tubing assembly and patient interface device in accordance with an exemplary embodiment of the present invention.

Referring now to FIG. 6, another exemplary embodiment of a tubing assembly 608 coupled to patient interface device 10 is illustrated. Tubing assembly 608 is of generally similar construction as tubing assembly 8 (FIGS. 1A and 1B) except each mounting tab 634 of tubing assembly 608 is adjustable with respect to tubing assembly 608 so as to allow for each mounting tab to be adjusted to best fit tubing assembly 608 to the head of a patient. More particularly, each mounting tab 634 is coupled to a respective tubular portion 614 in a manner such that each mounting tab can generally slide along a portion of the respective tubular portion 614, such as indicated by the arrows 601 in FIG. 6. As shown in the exploded detail view of FIG. 7, such "slidable coupling" between each mounting tab 634 and tubular portion 614 is accomplished via the interaction of a channel member 636 coupled to each mounting tab 634 which slidingly engages a correspondingly shaped rail member 638 coupled to each tubular portion 614. In the exemplary embodiment illustrated in FIG. 7, channel member 636 is formed generally as a c-shaped channel which is integrally formed with mounting tab 634 and rail member 638 is a generally t-shaped rail formed integrally with tubular portion 614 which is correspondingly sized to slidingly engage the interior of channel member 636. It is to be appreciated that other suitable sliding arrangements as well as fabrication methods may be employed without varying from the scope of the present invention.

Figure 7:
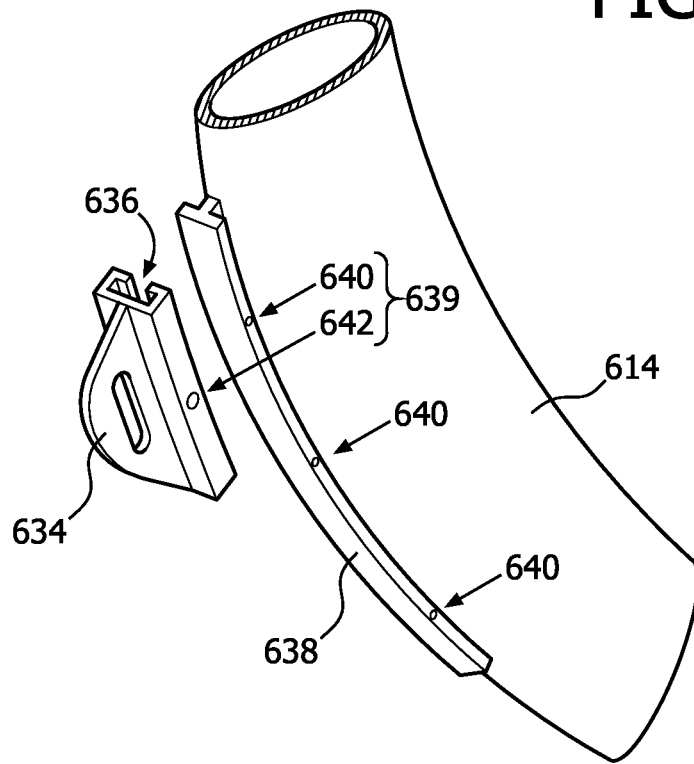
FIG. 7 is an exploded detail view of a portion of the tubing assembly of FIG. 6.

Continuing to refer to the detail view of FIG. 7, one or both of channel member 636 and/or rail member 638 may include a retention mechanism 639 for generally retaining mounting tab 634 in a desired position with respect to tubular portion 614. In the exemplary embodiment illustrated in FIG. 7, retention mechanism 639 includes a number (three are shown) of protrusions 640 which are spaced along and extend from rail member 638 and are engaged by an aperture 642 formed in channel member 636. It is to be appreciated, however, that other suitable arrangements may be used as a retention mechanism without varying from the scope of the present invention.

Figure 8:
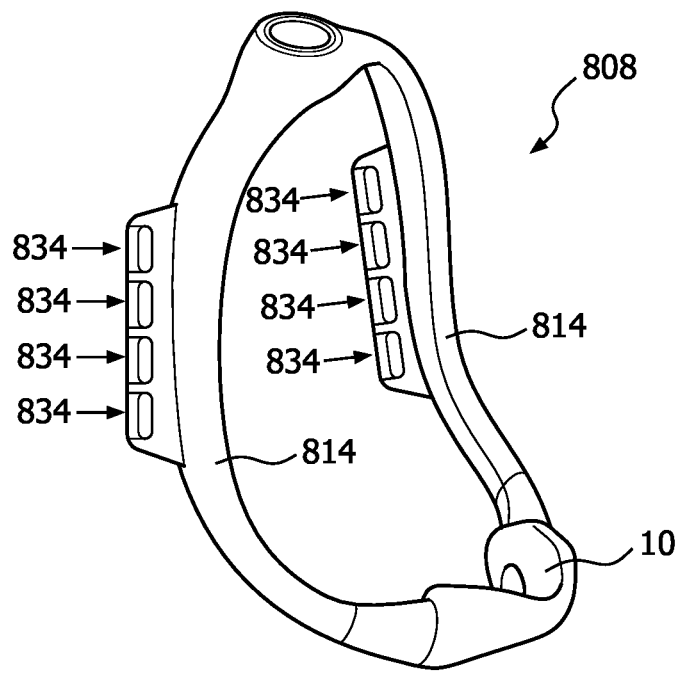
FIGS. 8 and 9 are isometric views of tubing assemblies and patient interface devices in accordance with exemplary embodiments of the present invention.
Figure 9:
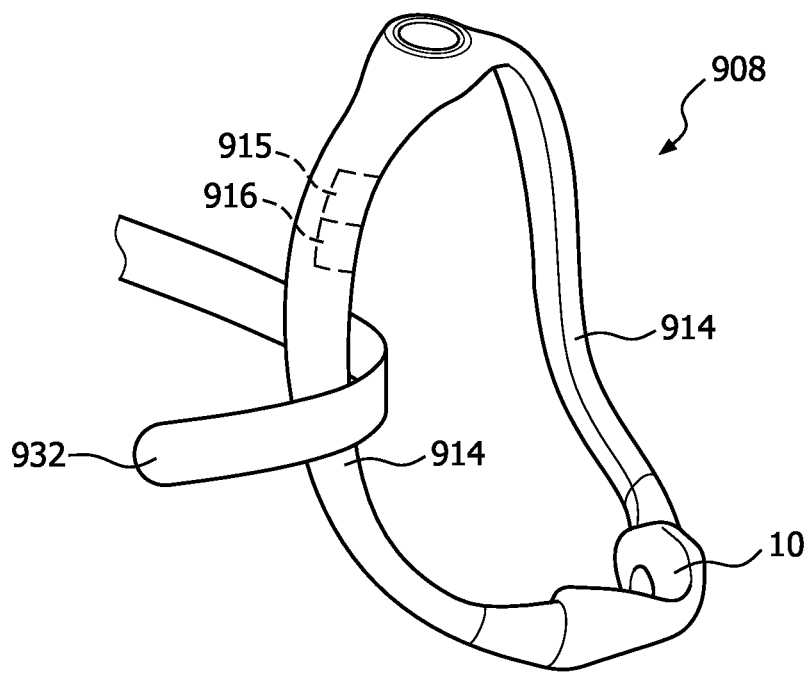

FIGS. 8 and 9 show further exemplary embodiments of tubing assemblies 808 and 908 which provide for adjustability of strap placement coupled to patient interface device 10. In the example shown in FIG. 8, each tubular portion 814 of tubing assembly 808 includes a plurality of mounting tabs 834 placed in various locations along tubular member 814 to which a rear strap member (not shown) may be selectively coupled via any suitable arrangement. In the example shown in FIG. 9, each tubular portion 914 of tubing assembly 908 is provided without any mounting tabs such that a rear strap member 932 may be generally placed anywhere along each tubular portion 914. In order to generally maintain rear strap 932 in a desired position with respect to tubular portion 914, each tubular portion 914 may further include one or more raised areas 915 (shown schematically in dashed line) or lowered areas 916 (shown schematically in dashed line). In addition to, or in place of such areas 915 and 916 strap member 932 may include a material (e.g., without limitation, a closed cell foam) which generally resists slippage along tubular portion 914.

Figure 10:
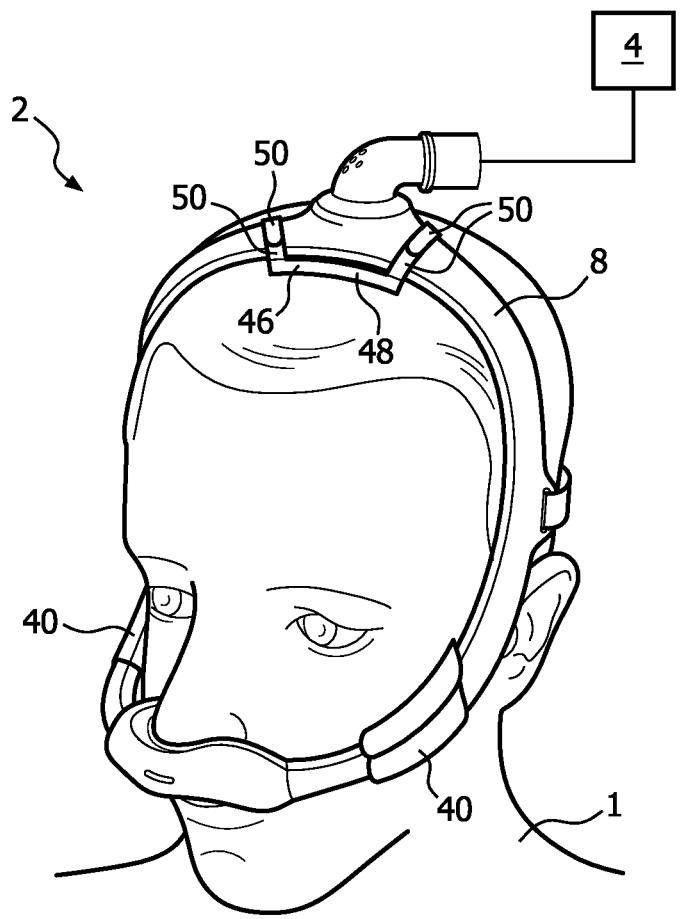
FIG. 10 is another partially schematic view of the respiratory interface system of FIG. 1 shown on the head of a patient along with a number of additional features in accordance with exemplary embodiments of the present invention.

In order to provide for an improved feel, one or more of the patient facing/engaging surfaces of tubing assembly 8 (as well as any tubing assembly in accordance with the present invention) may include an added feature formed thereon and/or coupled thereto. For example, in an exemplary embodiment such as shown in FIG. 10, tubing assembly 8 may include one or more sections of fabric wrap 40, securable via hook and loop (e.g., Velcro) or other suitable fastener may be provided to customize the feel of tubing assembly 8 to a particular patient's liking. In another exemplary embodiment, selected patient engaging portions of tubing assembly 8 were covered with a parylene coating which is applied to the silicone to give a silky feeling. Typically silicones are sticky but the parylene coating significantly reduces the friction of the material. Such coating is very comfortable on the skin as raw silicone can cause the skin to sweat and when coupled with a high friction material, it could cause skin irritation and skin breakdown. Simple textures have also been applied/formed on the silicone in other exemplary embodiments in order to improve/reduce friction of the silicon on exposed skin.

Figure 11:
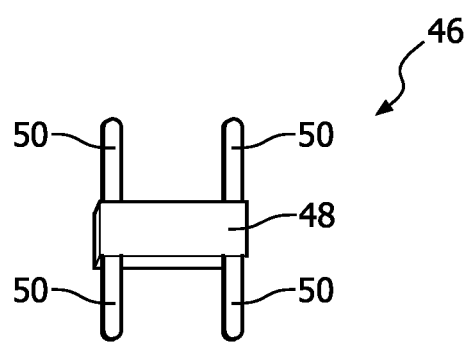
FIG. 11 is a generally plan view of a pad member in accordance with an exemplary embodiment of the present invention.

Continuing to refer to FIG. 10, as well as to FIG. 11, in an exemplary embodiment, one or more pad members 46 may be used to vary the feel of tubing assembly on the head of patient 1 and/or to better fit tubing assembly 8 to the head of patient 1. Each pad member 46 includes a central pad 48 and a number of arms 50 extending therefrom. Arms 50 are provided with suitable fasteners (not numbered) such that central pad 48 may be selectively coupled to a desired portion or portions of tubing assembly 8 via arms 50. Central pad 48 may be formed from foam, gel, silicone, fabric plastic, or any other suitable material or combination of materials.

FIGS. 12A and 12B show an exemplary embodiment of another element which may be selectively coupled to a tubing assembly, such as shown coupled to tubing assembly 8 in FIG. 13, in order to change one or both of the feel and/or appearance of tubing assembly 8. More particularly, FIGS. 12A and 12B illustrate an exemplary embodiment of an over-support member 54 which is structured to be generally fit over one of the tubular portions of a tubing assembly in accordance with the present invention. FIG. 13 illustrates an exemplary embodiment in which two over-support members 54 are coupled to tubular portions 14 of tubing assembly 8. Each over-support member 54 includes a channel 56 formed from silicone or other suitable material which is coupled to a patient facing portion 58. Patient facing portion 58 may include a particular surface texture or be formed from a separate material that presents a desirable feel for the patient. Accordingly, patient facing portion 58 may be formed from one or more of fabric, gel, a hydrophilic material, or other suitable material or combination of materials. The design process creates the shape and thickness that is required for structural stability that will allow over-support member 54 to generally hold onto tubular portion 14 without the need for any dedicated fasteners. Channel 56 defines an opening 60 along the entire length thereof which allows for over-support member 54 to be easily attached or removed from tubular portion 14. Opening 60 further allows for visual access to tubular portion 14 which is obstructed by a fabric wrap, such as fabric wrap 40 previously described. Frictional forces between channel 56 and tubular portion 14 limits movement of over-support member 54 with respect to tubular portion 14.

The material used for patient facing portion 58 may be generally disposed so as to only cover the area actually facing the patient, such as shown in the exemplary embodiment of FIGS. 12A, 12B and 13, or such material may cover beyond such patient-facing surface in order to provide a reduced friction surface that can readily glide more easily over a pillow during sleep. In order to vary the flexibility of over-support member 54, a number of cut-outs 62 may be provided in channel 56.

Having thus described some exemplary embodiments for improving the feel and/or look of a tubing assembly in accordance with the present invention, some exemplary embodiments for adjusting the sizing of a tubing assembly in accordance with the present invention will now be described.

Figure 14:
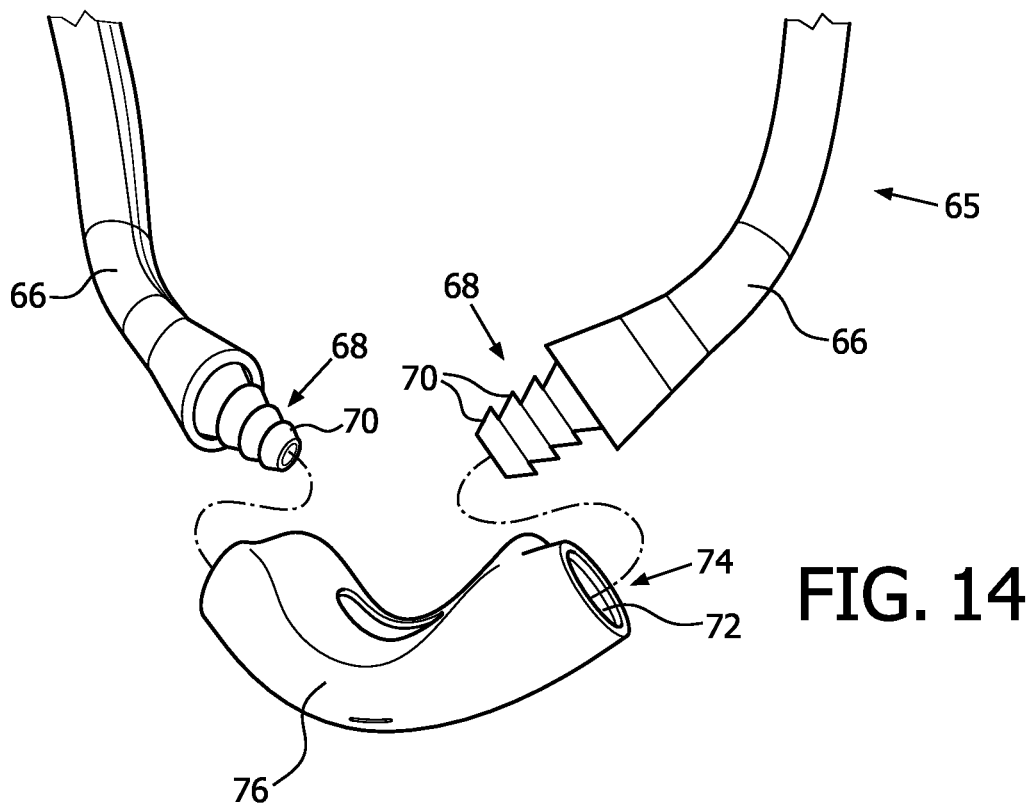
FIGS. 14 and 15 are exploded isometric views of portions of tubing assemblies and patient interface devices which provide for adjustable sizing of the tubing assemblies in accordance with exemplary embodiments of the present invention.
Figure 15:
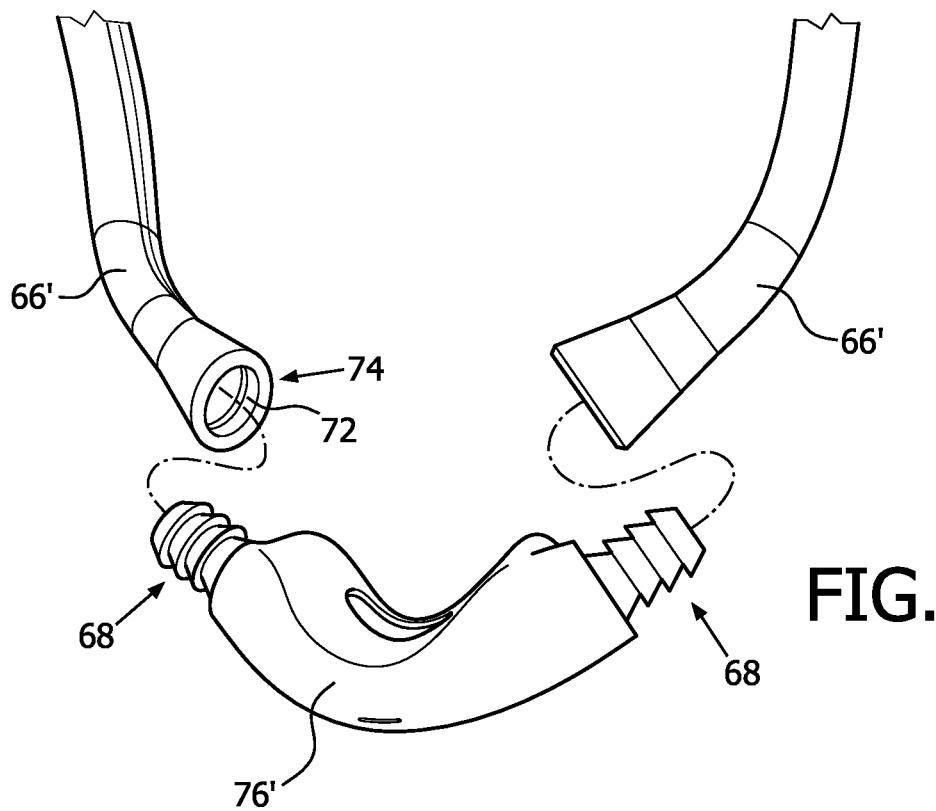

FIGS. 14 and 15 show exemplary embodiments of arrangements which offer adjustable sizing of a tubing assembly 65 (only partially shown) of generally similar construction as other tubing assemblies in accordance with the present invention except tubing assembly 65 includes an adjustment portion 68 which extends from the end of each tubular portion 66. Each adjustment portion 68 includes a number (three are shown) of flared segments 70, each of generally similar size and shape, which are structured to engage a correspondingly shaped receiving portion 72 formed in an opening 74 of patient interface device 76. More particularly, each flared segment 70 engages receiving portion 72 in a click-like fashion such that a desired one flared segments 70 may be selectively clicked into engagement with receiving portion 72. Accordingly, the exemplary embodiment shown in FIG. 14 provides for each tubular portion 66 to be disposed in one of three (corresponding to the three flared segments 70) positions with respect to patient interface device 76. FIG. 15 shows an exemplary embodiment in accordance with the present invention which is similar to that shown in FIG. 14 except having adjustment portions 68 and receiving portions 72 which are reversed from the arrangement shown in FIG. 14. It is to be appreciated that one or more of the shape and quantity of flared segments may be varied without varying from the scope of the present invention.

Figure 16A:
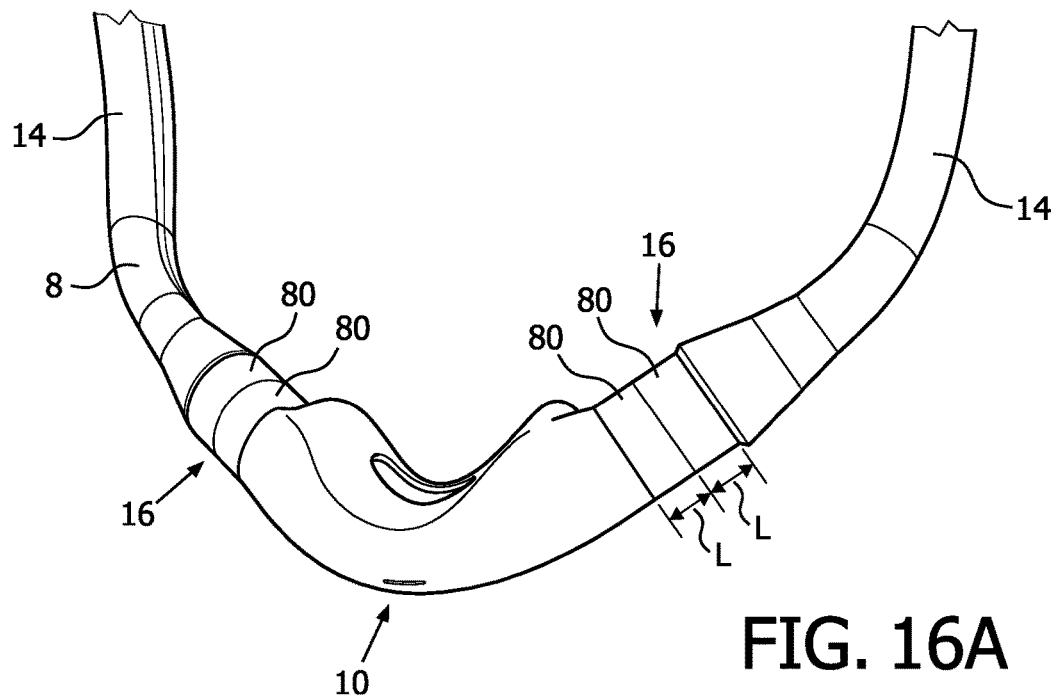
FIGS. 16A and 16B, respectively, show assembled and exploded isometric views of portions of a tubing assembly and patient interface device which provides for adjustable sizing of the tubing assembly via a modular mechanism in accordance with an exemplary embodiment of the present invention.
Figure 16B:
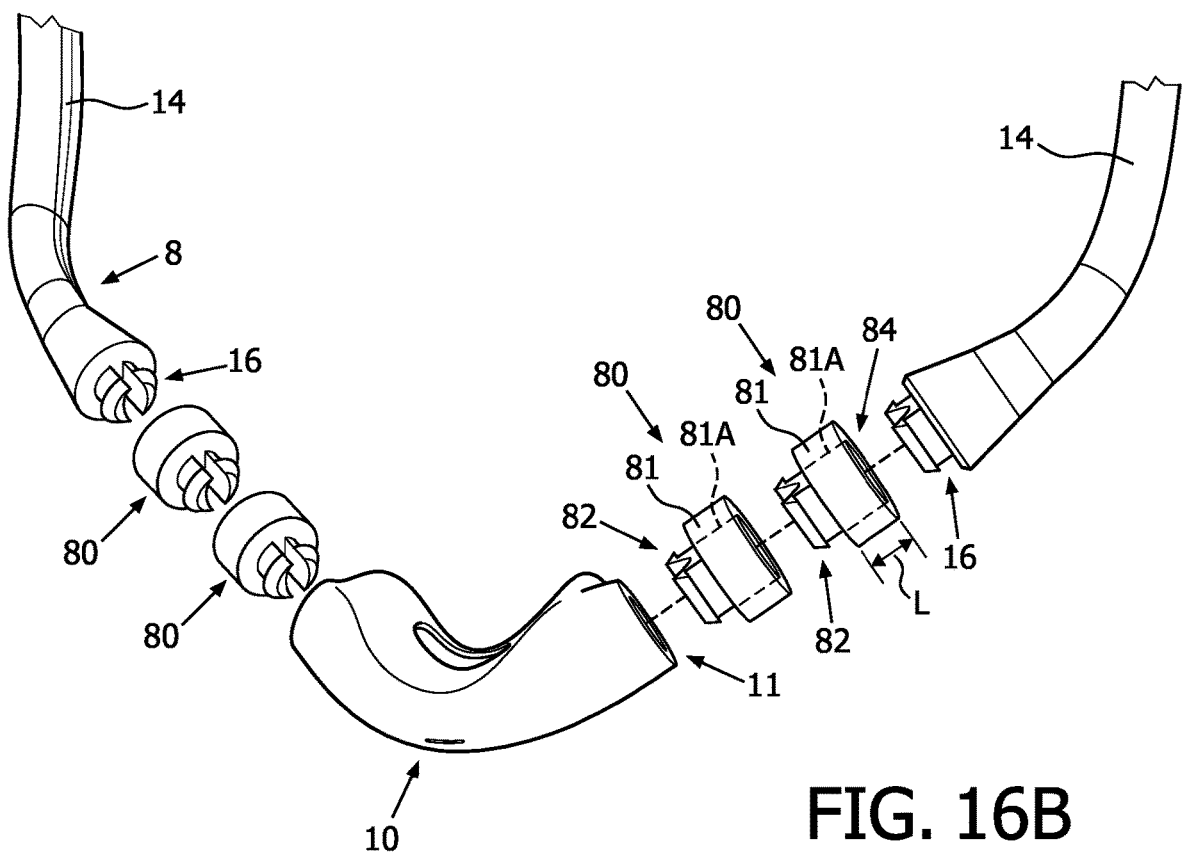

FIGS. 16A and 16B, respectively, show assembled and exploded views of an exemplary embodiment of a modular adjustment arrangement in accordance with the present invention. More particularly, the embodiment shown I FIGS. 16A and 16B utilizes a number of tubular adjustment members 80 which may be selectively disposed in between distal end 16 of each tubular portion 14 of tubing assembly 8 and patient interface device 10 (or any other combination of tubing assembly and patient interface device in accordance with the present invention). Referring to FIG. 16B, each adjustment member 80 includes a body 81 which defines a hollow passage 81A therethrough and is of a predetermined length L. Each adjustment member 80 includes a protruding portion 82 extending from a first end of body 81, which is of similar form as distal end 16 of tubular portion 14, and a receptacle portion 84 defined in an opposite end of body 81, which is of similar form as an end portion 11 of patient interface device 10. Accordingly, each protruding portion 82 may readily be snap fit (or conversely unsnapped) from one of receptacle portions 84 in a manner like fitting end 16 to end 11 of patient interface device 10.

Through such arrangement, the relative spacing between end 16 of each tubular portion 14 and patient interface device 10 can be adjusted in increments of predetermined distance L without adversely affecting a flow of gas from tubular portion 14 to patient interface device 10. It is to be appreciated that predetermined distance L, as well as the general form of each of protruding and receptacle portions 82 and 84 may be varied to meet the requirements of a particular application without varying from the scope of the present invention. It is also to be appreciated that the arrangement of protruding and receptacle portions 82 and 84 may be reversed (i.e., such that receptacle portion 84 are formed in tubular portions 14 and protruding portions 82 extend from patient interface device 10 without varying from the scope of the present invention.

Figure 17:
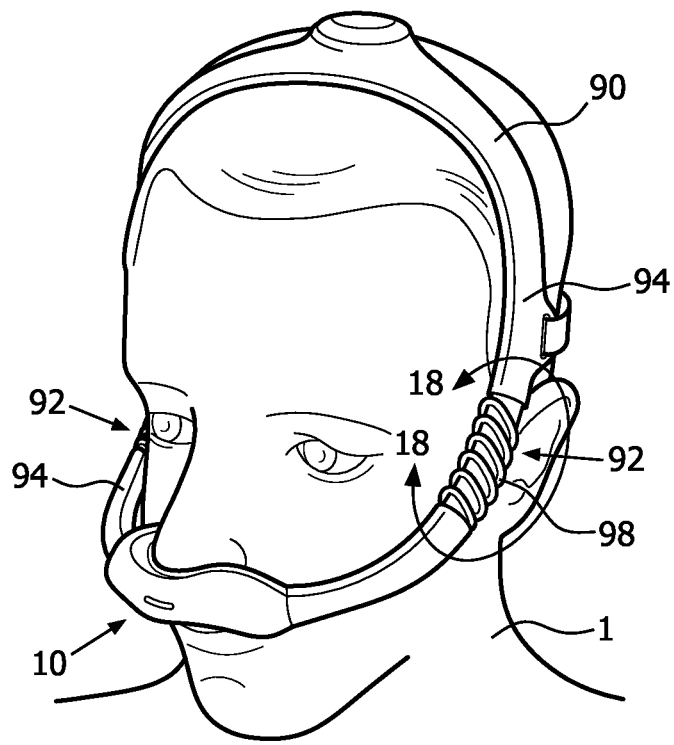
FIG. 17 is a view of a tubing assembly and patient interface device including integral adjustment portions in accordance with an exemplary embodiment of the present invention shown disposed on the head of a patient.
Figure 18:
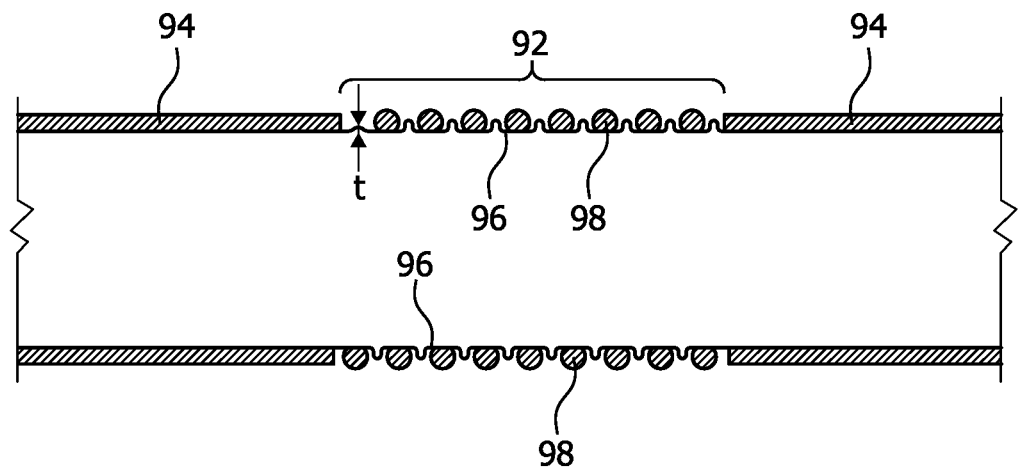
FIG. 18 is a sectional view of one of the adjustment portions of FIG. 17.

An exemplary embodiment of a tubing assembly 90 in accordance with the present invention having integral adjustment portions 92, one disposed in each of tubular portions 94, is illustrated in FIG. 17 and in a schematic sectional view FIG. 18. Referring to FIG. 18, each adjustment portion 92 includes a stretch portion 96 which in the exemplary embodiment illustrated in FIG. 18 is formed as a thinned portion of tubular portion 94. Stretch portion 96 is structured to elongate in order to accommodate patient heads of different sizes. Stretch portion 96 can be disposed generally anywhere, and in one or more locations, along tubular portion 94 to provide stretch as needed for patient head geometry. Stretch portion 96 may also be formed from various materials with different stretch characteristics. As an example, a low durometer material may be overmolded to provide more elasticity. As another example, the characteristics of how stretch portion 96 stretches may varied by varying the thickness t of stretch portion 96. In order to prevent collapse, adjustment portion 92 may further include a support element 98, such as the generally coil-shaped member shown in FIGS. 17 and 18 which generally wraps around stretch portion 96.

Figure 19A:
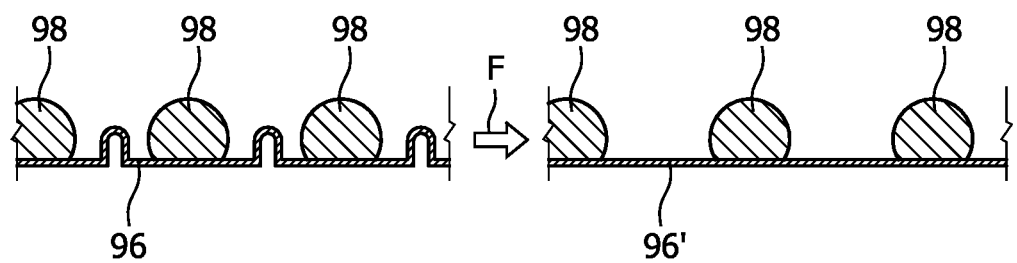
FIGS. 19A and 19B are sectional views of portions of two exemplary embodiments of adjustment portions in accordance with the present invention showing each portion in relaxed and stretched positions.
Figure 19B:
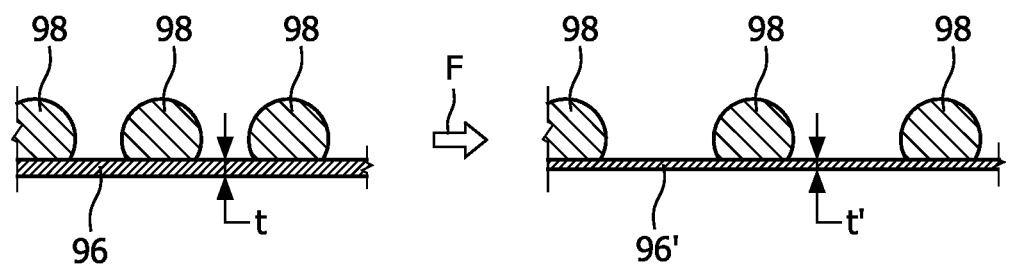

FIGS. 19A and 19B show sectional views of examples of how two different exemplary embodiments of stretch portion 96 of adjustment portion 92 distort (such as shown by 96') when a force F is applied to stretch tubular portion 94.

Figure 20:
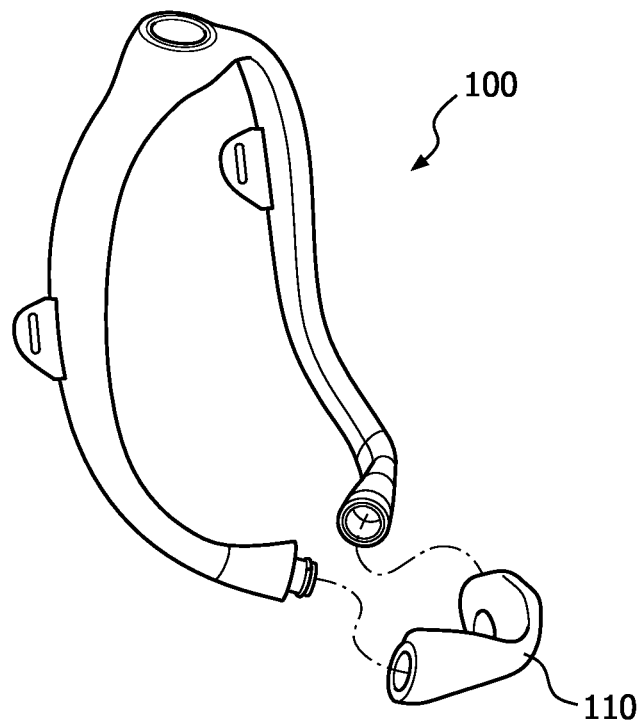
FIG. 20 is an exploded view of a tubing assembly and patient interface device in accordance with an exemplary embodiment of the present invention which provides for the adjustment of the angular positioning of the patient interface device with respect to the tubing assembly.
Figure 21:
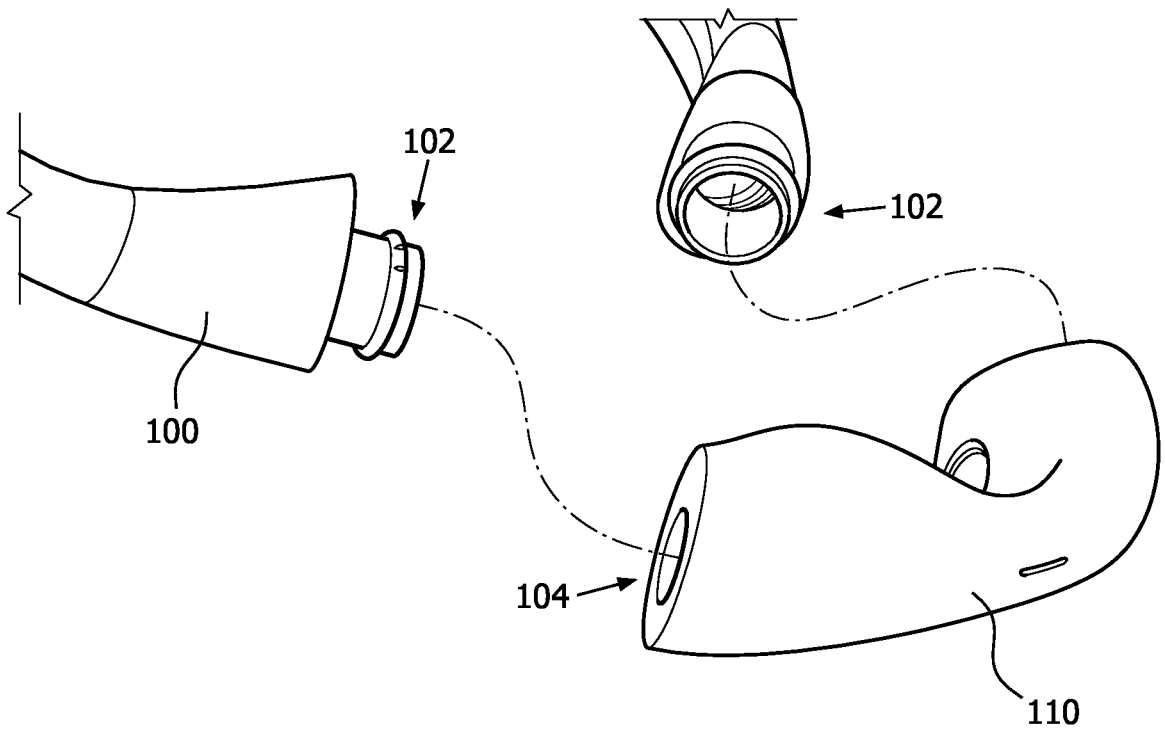
FIG. 21 is an enlarged view of a portion of the exploded view of FIG. 20.
Figure 22A:
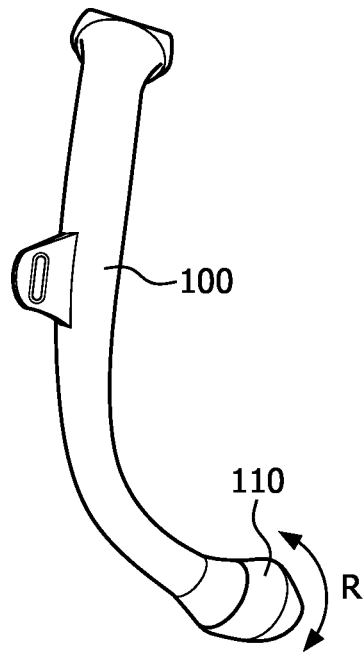
FIGS. 22A and 22B are assembled side elevation views of the tubing assembly and patient interface device of FIG. 20.
Figure 22B:
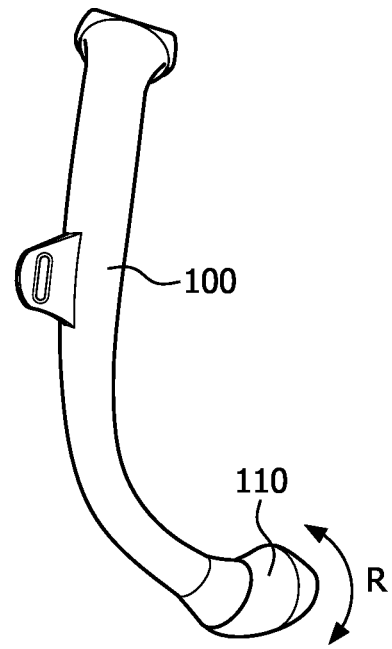

FIGS. 20 and 21 show an exemplary embodiment of a tubing assembly 100 which provides for the angular positioning of a patient interface device 110 coupled thereto to be selectively adjusted. Such adjustability is provided via the interaction of a circular protruding member 102 which interacts with a correspondingly shaped aperture 104 into which protruding member 102 may be snap fit in a manner such that patient interface device 110 may rotate generally up and down, such as shown by arrow R in the side view of FIGS. 22A and 22B, with respect to tubing assembly 100.

Figure 23A:
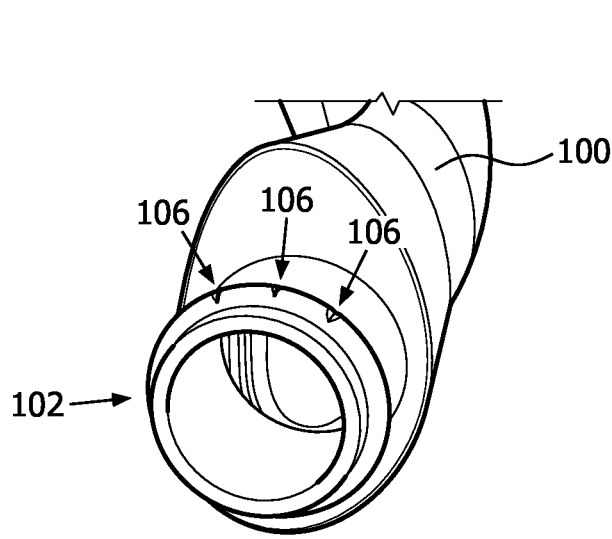
FIGS. 23A and 23B are details views of the end of a tubing assembly in accordance with an exemplary embodiment of the present invention.
Figure 23B:
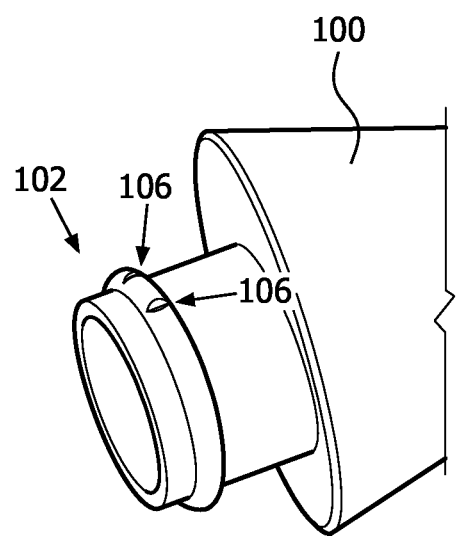

Although shown with protruding members 102 extending from tubing assembly 100 and apertures 104 formed in patient interface device 110, it is to be appreciated that such features may be reversed (i.e., protruding members 102 extending from tubing assembly patient interface device 110 and apertures 104 formed in tubing assembly 100) without varying from the scope of the present invention. In order to generally maintain the angular positioning between patient interface device 110 and tubing assembly 100, an angle lock mechanism may be provided which generally restricts rotation of patient interface device 110 with respect to tubing assembly 100. An exemplary embodiment of such mechanism is illustrated in FIGS. 23A and 23B in the form of notches 106 which are structured to interact with a protruding portion (not shown) which extends into aperture 104.

It can be appreciated that the present invention provides Accordingly, mechanisms for customizing one or more of the size and feel of such headgear to meet the needs of particular patients.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A tubing assembly for use with a patient interface device in delivering a flow of breathing gas to the airway of a user, the tubing assembly comprising:
    a manifold portion structured to be disposed generally at the top of the user's head and adapted to be coupled to a conduit carrying the flow of breathing gas; and
    a number of tubular portions, each tubular portion extending from the manifold portion to a distal end which is structured to be coupled to the patient interface device, each tubular portion being structured to communicate the flow of breathing gas from the manifold portion to the patient interface device, wherein each tubular portion comprises an adjustment element which provides for a characteristic of the tubular portion to be selectively varied, wherein each tubular portion comprises a mounting tab adjustably coupled thereto such that the mounting tab is selectively movable along a length of the tubular portion, each mounting tab being structured to receive a portion of a strap member for securing the tubing assembly to the head of the user, and wherein each mounting tab is slidably coupled to one of the tubular portions via an interaction of a channel member and a rail member.

2. The tubing assembly of claim 1, wherein the rail member is disposed on the tubular portion and the channel is defined in the mounting assembly.

* * * * *